United States Patent [19]

Neil

[11] Patent Number: 5,458,141
[45] Date of Patent: Oct. 17, 1995

[54] ABRASIVE SKIN ELECTRODE

[75] Inventor: Brian K. Neil, Issaquah, Wash.

[73] Assignee: Quinton Instrument Company, Bothell, Wash.

[21] Appl. No.: 101,869

[22] Filed: Aug. 4, 1993

[51] Int. Cl.$^6$ .................................................. A61B 5/0416
[52] U.S. Cl. ............................................................ 128/641
[58] Field of Search .................................... 128/639–641, 128/644; 607/149, 152

[56] References Cited

U.S. PATENT DOCUMENTS

| | | |
|---|---|---|
| Re. 32,724 | 8/1988 | Cartmell . |
| 2,621,657 | 12/1952 | Leech ........................................ 128/644 |
| 4,029,086 | 6/1977 | Corasanti . |
| 4,155,354 | 5/1979 | Rasmussen . |
| 4,257,424 | 3/1981 | Cartmell . |
| 4,265,253 | 5/1981 | Abraham . |
| 4,270,544 | 6/1981 | Gilden et al. . |
| 4,274,419 | 6/1981 | Tam et al. . |
| 4,300,575 | 11/1981 | Wilson . |
| 4,311,152 | 1/1982 | Modes et al. . |
| 4,319,579 | 3/1982 | Cartmell . |
| 4,331,153 | 5/1982 | Healy . |
| 4,488,557 | 12/1984 | Engel . |
| 4,524,087 | 6/1985 | Engel . |
| 4,539,996 | 9/1985 | Engel . |
| 4,559,950 | 12/1985 | Vaughan et al. . |
| 4,595,013 | 6/1986 | Jones et al. . |
| 4,674,511 | 6/1987 | Cartmell . |
| 4,679,564 | 7/1987 | Sessions . |
| 4,700,710 | 10/1987 | Hoffman . |
| 4,706,680 | 11/1987 | Keusch et al. . |
| 4,738,263 | 4/1988 | Seebach et al. . |
| 4,757,817 | 7/1988 | Healy . |
| 4,768,514 | 9/1988 | De Marzo . |
| 4,777,954 | 10/1988 | Keusch et al. . |
| 4,798,208 | 1/1989 | Faasse, Jr. . |
| 4,838,273 | 6/1989 | Cartmell . |
| 4,934,383 | 6/1990 | Glumac . |
| 5,114,424 | 5/1992 | Hagen et al. . |

FOREIGN PATENT DOCUMENTS 2240928   8/1991   United Kingdom .

OTHER PUBLICATIONS

3M Co., "3M announces the New High Performance Red Dot® Monitoring Electrode" brochure, date unknown.
Ver–Med, "Ver–Med Breathable Electrode" brochure, date unknown.
Ferris Mfg., Co., "Ferris Trace–Itt Pregelled Disposable Pads for the EKG Lab" literature, date unknown.
Medtronic Andover Medical, "ClearTrace™ Monitoring Electrode with Adhesive Gel" literature, date unknown.

*Primary Examiner*—Lee S. Cohen
*Attorney, Agent, or Firm*—Andrew J. Beck; Montgomery W. Smith; Richard D. Allison

[57] ABSTRACT

A medical electrode and skin preparation device is adapted to be secured to the skin of a patient and is designed to prepare the skin by abrasion or penetration of the epidermal layer of the skin in contact with the conductive means of the electrode after the electrode is secured in place on the skin. The electrode includes a penetrating device associated with a conductor capable of transmitting biopotential events for recording, with the conductor being retained by an adhesive member which secures the electrode to the skin of the patient. The penetration device in contact with the skin is movable relative to the skin of the patient and a holder by an applicator gun to abrade or penetrate the epidermal layer of skin after the electrode is placed on the skin. Uniform skin preparation is achieved by a flexible screen member and an electrolyte gel reservoir on the electrode and an applicator gun which minimizes motion artifacts arising from skin potential variations.

18 Claims, 5 Drawing Sheets

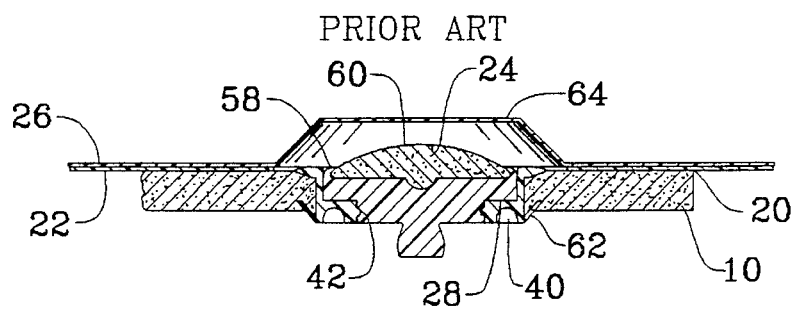
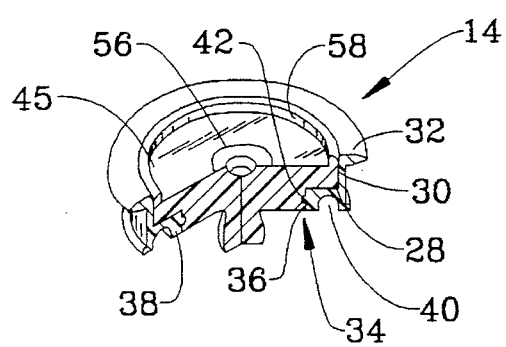
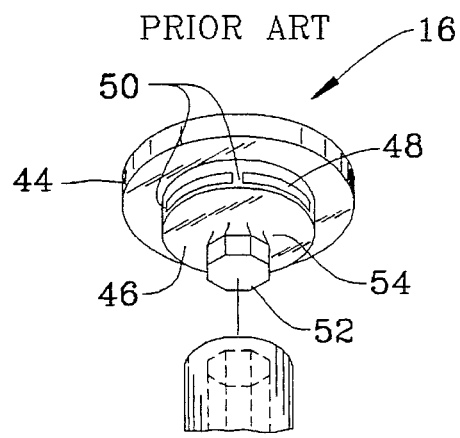
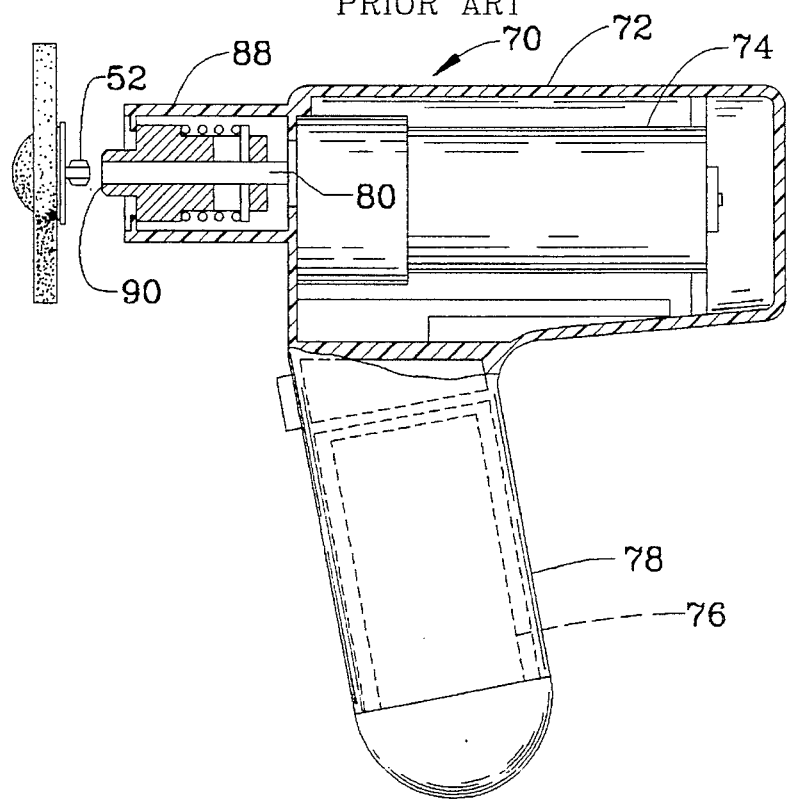

ABRASIVE SKIN ELECTRODE

FIELD OF THE INVENTION

This invention relates to an improved medical electrode which performs skin preparation in addition to sensing and recording biopotential events. The electrode, after application to the skin, is employed to abrade or penetrate the epidermal layer of the skin for minimizing motion artifacts.

BACKGROUND OF THE INVENTION

Motion artifacts have long been a problem during the measurement of biopotentials, particularly in long-term electrocardiogram (ECG) monitoring of coronary care patients and in exercise (stress) ECG's. Motion artifacts can be defined as motion induced fluctuation of the electrical potential across the skin of the patient. Motion artifacts manifest themselves as electrical interference which is often superimposed on the desired biopotential signal and minimizes the usefulness of the biopotential signal for diagnostic and clinical purposes. Motion artifacts are generally caused by the movement of the patient relative to the electrode applied to the patient's skin, thereby disturbing the skin potential and creating extraneous readouts on the ECG monitor which either mask or cause a shift in the baseline of the desired biopotential signal.

It is well known that light abrasion of the skin reduces the electrical potential and minimizes the impedance of the skin of the patient, thereby reducing motion artifacts and improving signal or trace quality of the biopotential signal. Although there are many commercially available surface mounted electrodes for cardiac monitoring described in the literature, reliable signals or trace results from these electrodes in highly dependent on adequate skin preparation prior to application of the electrodes. Proper skin preparation is time consuming because typical stress electro-cardiograms usually require between three and 12 electrodes and typically use about 10 electrodes. Skin preparation is normally necessary to remove the epidermal layer of the skin of the patient and is carried out in a variety of ways. The most common method of preparing the skin is to rub the patient's skin with a gritty material contained in a carrier or to rub the patient's skin with a rough surfaced material to which an antiseptic such as alcohol or other solvent is applied. After briskly rubbing the skin, the skin is dried and again rubbed with a dry cloth. If, after the electrodes are applied, a proper signal or trace is not obtained from one or more of the electrodes, the malfunctioning electrodes must be identified, removed and the skin must be prepared again. The electrodes are then reapplied to the skin of the patient, and this procedure is repeated until an adequate and accurate signal is received from each electrode. The effectiveness of the skin preparation is highly dependent on the technique used as well as the level of skill of the person preparing the skin. Predictably, the effectiveness of the skin preparation in this uncontrolled manner is highly variable between electrode locations as well as between patients.

U.S. Pat. Nos. 4,274,419 and 4,311,152 are owned by the assignee of the present invention and disclose a surface mounted medical electrode suitable for recording biopotential measurements in which the electrode is first applied to the patient, and then the skin of the patient is prepared. Such an approach markedly reduces the time consumed in the application of electrodes for recording biopotential events. Also, more reliable, accurate and uniform signals are obtained since the amount and type of skin preparation for each electrode is generally uniform.

SUMMARY OF THE INVENTION

It is a primary object of this invention to provide a medical electrode which performs skin preparation after application of the electrode to the desired location on the skin of the patient and before the recording of biopotential events.

The preferred form of the electrode of the present invention includes a rotatable conductive means as well as a rotatable penetration means associated therewith for the abrasion of the epidermal layer of skin. Both the conductive means and penetration means may be rotated after application of the electrode to the skin of the patient to prepare the skin and thereby minimize motion artifacts arising from skin potential variations and skin impedance. The electrode of the present invention is preferably pre-gelled and disposable although non pre-gelled or reusable electrodes are believed to be within the scope of the present invention.

In the present invention, the conductive means of the electrode retains the epidermal penetrating means therein and is preferably provided with an electrolyte such as a gel material in a recess formed between the conductive means and penetrating means. The conductive means is secured for rotational movement relative to an adhesive coated sheet member which is used to adhere the electrode to the skin. When the electrode is pre-gelled, it may be provided with a removable cover for protecting the adhesive coated sheet member and the penetrating means having the electrolyte gel therein. In a preferred form of the present invention, the conductive means is a carbon based, silver plated center member, and the penetrating means is preferably a flexible screen-type member.

It is a further object of this invention to provide a surface mounted medical electrode capable of a more uniform and consistent skin preparation between individual electrodes and patients.

It is a further object of the present invention to provide an electrode which minimizes the interference of motion artifacts and skin impedance with biopotential signals.

It is a further object of this invention to provide a surface mounted medical electrode having a rotatable abrasive member for abrading the skin after application of the electrode to the patient.

Another object of this invention is to provide a surface mounted electrode which eliminates technique variability in skin preparation, thereby minimizing motion artifact while decreasing the likelihood that the skin of the patient will be abraded excessively.

Yet another object of the present invention is to provide an electrode which forms a gel column between the circumferential housing, the electrically conductive center member and the skin of the patient to maintain electrical contact between the skin of the patient and the center member during use of the electrode as well as reducing the time necessary for application of an electrode to a patient.

It is yet another object of the present invention to provide a surface mounted electrode which is inexpensive to manufacture and easy to assemble.

BRIEF DESCRIPTION OF THE DRAWINGS

FIGS. 2A and 2B are cross-sectional views of the prior art electrode of FIG. 1;

FIG. 3 is a perspective view of the projecting stud of the prior art conductive member and the coupler of the prior art applicator gun illustrating the manner in which the applicator gun is connected to the stud of the prior art electrode of FIG. 1 for rotation of the conductive member by the applicator gun;

FIG. 4 is a schematic view of a prior art applicator gun used to drive the movable conductive element and abrasive member of the prior art electrode of FIG. 1 and the electrode of the present invention to perform skin preparation.

DESCRIPTION OF THE PREFERRED EMBODIMENTS

Figure 1:
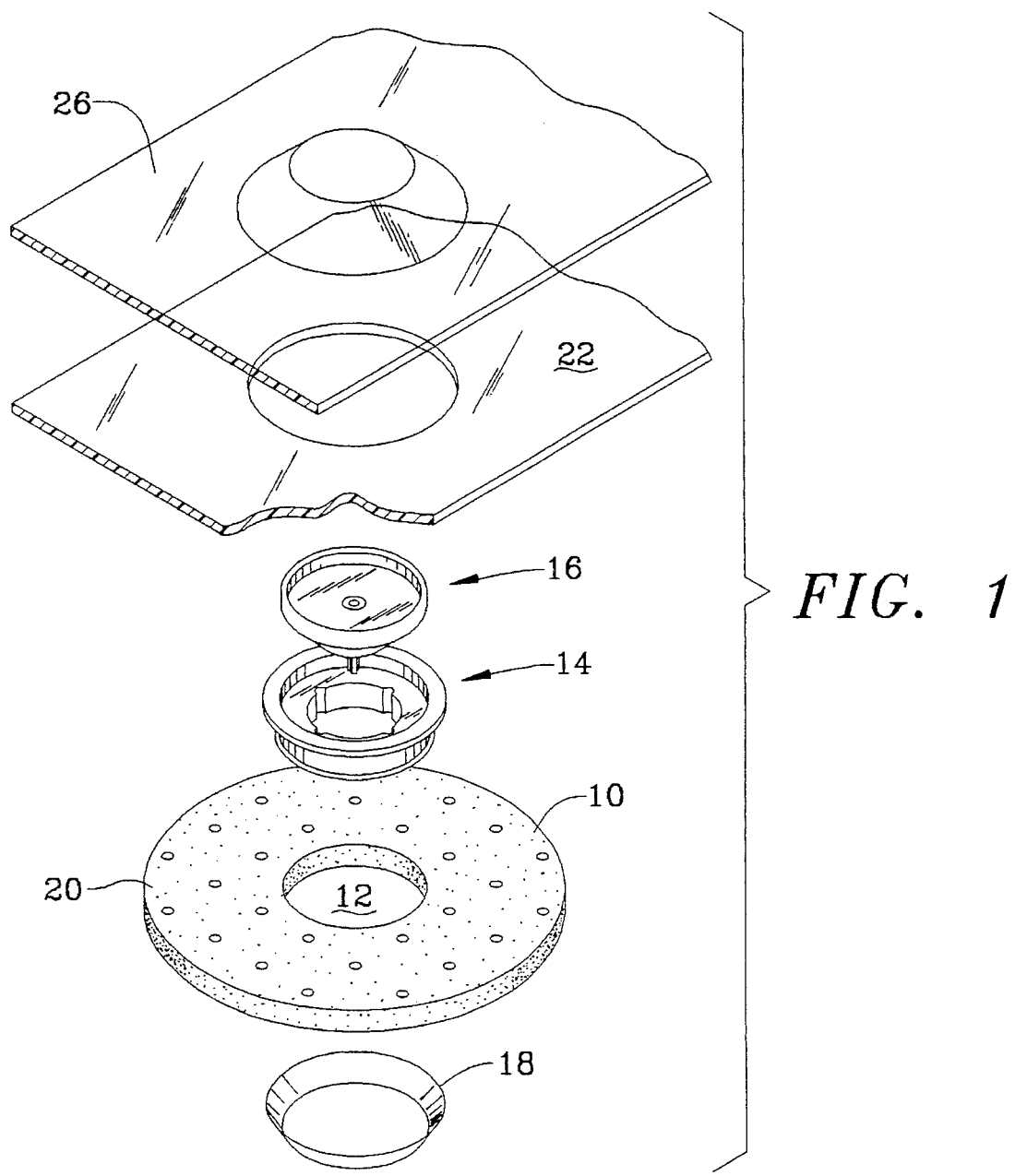
FIG. 1 is an exploded view of a prior art surface mounted medical electrode, illustrating the components which make up the electrode except for the abrasive electrolyte-containing member.

FIGS. 1–4 illustrate a surface mounted electrode and applicator gun 70 of the prior art which are more fully set forth in U.S. Pat. Nos. 4,274,419 and 4,311,152. These patents are commonly owned by the assignee of the present invention and are incorporated herein as if fully set forth below. The prior art electrodes of FIGS. 1–6 are described herein to provide a better understanding of the differences in structure and function of the prior art electrodes and the present invention. The prior art electrode shown in FIGS. 1–4 generally consists of a circular sheet member 10 having an annular cutout portion 12 in the center thereof into which a collar 14 is inserted. The collar 14 is shaped to hold an electrically conductive member 16 therein. A ring member 18 is further employed to clamp around the upper portion of the collar 14. The sheet member 10 is coated on one side with a skin adhesive layer 20. The adhesive is protected during storage with a protective cover 22. A spongy abrasive member 24 (see FIG. 2) is provided with an electrolyte gel thereon and is placed in contact with the conductive member 16. The abrasive member 24 is protected during storage with the protective cover 26.

The prior art collar 14 has the general configuration of an inverted hat having a flat base 28 and a vertical wall 30 normal and integral with the flat base 28 terminating in a contoured flange 32. The flat base 28 has an annular opening 34 in the center thereof with a diameter less than the diameter of the inner wall 30. Around the annular opening 34, is a vertical wall 36 having slots 38 cut therein about every 90 degrees. The walls 30 and 36 extend above the plane of the base 28 leaving a channel 40 therebetween. The collar 14 is generally molded from a semi-flexible, nonconductive plastic material such as an acetate-based material, nylon, polyester, polyethylene or polypropylene. The wall 36 is made sufficiently thin so that it can be flexed under pressure. The diameter of the collar 14 is substantially greater than its height. The inner periphery of the wall 36 is provided with a ridge 42 which functions to retain the conductive member therein.

The prior art electrically conductive member 16 is adapted to be snapped into the collar 14. The electrically conductive member 16 may be manufactured from a synthetic resin impregnated with carbon from a suitable electrically conductive metal or metal containing material or other suitable electrically conductive material. As shown in FIGS. 2 and 3, the electrically conductive member 16 includes a lower portion 44 having a textured convex lower surface 45 and a thickness substantially equal to the depth of the cup formed by the flange 32, wall 30 and base 28 of the collar. Integral with the lower portion 44 is an upper portion 46 of reduced diameter relative to the lower portion. The upper portion 46 has a diameter equal to that of the annular opening 34 in the collar 14. The circumference of the upper portion has a slot 48 therein which is interrupted by detents 50 positioned normal to the slot 48. The slot 48 of the conductive member 16 receives the ridge 42 in the wall 36 of the collar 14 to prevent the conductive member from moving vertically within the collar. The detents 50 of the conductive member 16 engage in the slots 38 in the flexible wall 36 of the collar 14 to prevent the conductive member from being rotated except by the predetermined torque/force of the applicator gun 70. A downwardly extending stud 52 provided on the bottom of the conductive member 16 preferably includes a polygonal outer surface 54 so that the coupler of the applicator gun can be drivingly secured over the stud to rotate the conductive member 16.

The prior art penetrating means for abrading or penetrating the epidermal layer of skin is a separate porous abrasive member 24 as illustrated in FIGS. 2A and 4. The abrasive member 24 is a generally fibrous pad incorporating abrasive fibers and having a convexly curved surface 60 and a diameter substantially the same as the diameter of the lower portion 44 of the conductive member 16. A flange 58 is folded against the edges of the abrasive member 24 to clamp the abrasive member 24 in the conductive member 16. The prior art abrasive member 24 is loaded with electrolyte gel so that when the electrode is applied to the skin, the electrolyte gel provides electrical contact between the skin and the conductive member 16.

The assembled collar 14, conductive member 16 and abrasive member 24 are snapped together and placed in the annular opening 12 of the adhesive coated sheet member 10. The adhesive coating 20 contacts the upper surface of the flange 32 of the collar 14 to secure the collar 14 in place relative to the sheet member. A snap ring 18 as shown in FIG. 1 is snapped over the wall 30 of the collar. The snap ring 18 is held in place by a ridge 62 extending around the outer terminating edge of the wall 30 of the collar 14.

FIGS. 3 and 4 generally illustrate the prior art applicator gun 70 which is used with the electrode of the present invention described below. The applicator gun 70 generally includes a housing 72 within which is mounted an electric motor 74 driven by AC or DC current from a suitable current source. The motor illustrated is driven by a rechargeable battery 76 held in place in a quickly disconnectable case 78 which also serves as the handle of the applicator. The lower end of the case includes recessed electrical contacts 79 for battery recharging. The motor has a shaft 80 to which a coupler 88 is attached. The coupler 88 includes a polygonal recess 90 thereon which is shaped to receive the specifically shaped stud 52 of the electrode therein.

Figure 5:
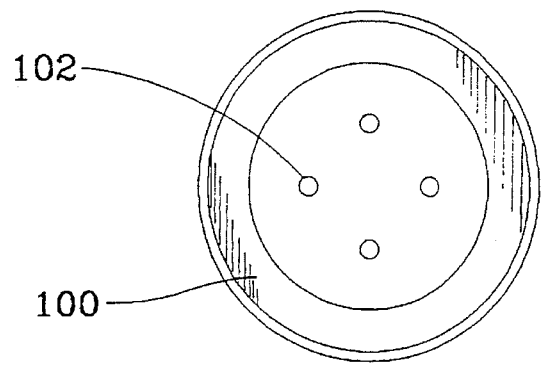
FIG. 5 is a perspective view, partially in cross section, showing a further prior art electrode.
Figure 6:
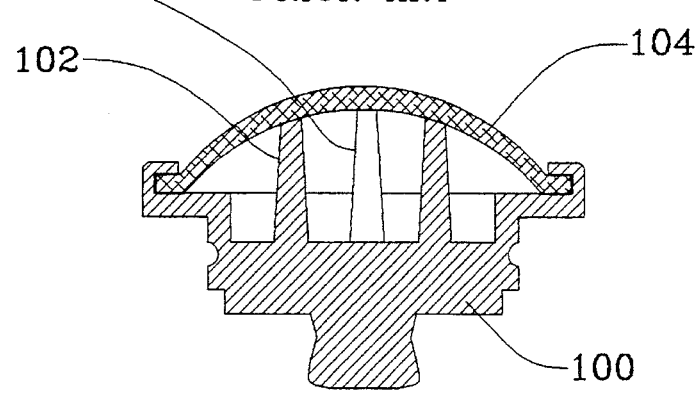
FIG. 6 is an elevated view of the prior art electrode of FIG. 5 illustrating the mesh screen and gel removed therefrom.
Figure 8:
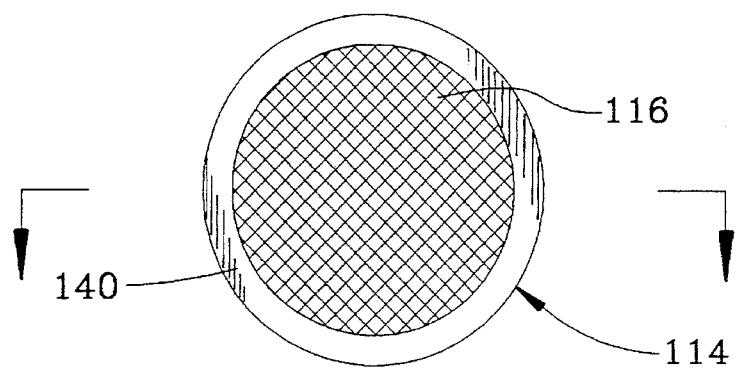
FIG. 8 is an elevated view of the assembled electrode of the present invention.

FIGS. 5 and 6 are illustrative of a further variation of a prior art electrode. For the sake of brevity, like numbers have been added to like members described above with respect to the prior art electrode shown in FIGS. 1–4. In this prior art electrode, the conductor member 100 is modified to include four equally spaced apart post members 102 extending therefrom. The conductor member 100 of this electrode includes a silver chloride paint sprayed thereon to increase the electrical conductivity between the patient, electrolyte gel and conductor member 100. The post members 102 in this electrode provide rigid support for the mesh screen 104 which replaces the abrasive member 24 of the prior art electrode described above. In this electrode the electrolyte gel (not shown) is positioned between the conduction member 100 and the mesh screen 104. In operation, the post members 102 rigidly support the mesh screen 104 to prevent the flexing of the mesh screen 104 as the skin of the patient is prepared. Additionally, the rigid support of the mesh screen 104 by the post members 102 inhibits the flow of the electrolyte gel (not shown) during use.

FIGS. 7–12 are illustrative of the preferred forms of the present invention. The electrode 110 of the present invention is preferably a radiolucent member which consists generally of an electrically conductive center member 112 which is received in a circumferential housing 114. The housing 114 includes a flexible screen member 116 received therein on the side of the housing 114 opposite to the center member 112. As with the prior art electrodes described above, the electrode 100 of the present invention further includes an adhesive coated sheet member 118 surrounding a retaining ring 150. The sheet member 118 is preferably formed of a cross linked polyethylene foam having an adhesive thereon to facilitate the attachment of the electrode 100 to the skin of the patient. Prior to use, the adhesive surface of the sheet member 118 is protected by a paper-like protective cover 120, and the surface of the electrode is further protected in a tray-like package (not shown) or by a further protective cover 121.

Figure 7:
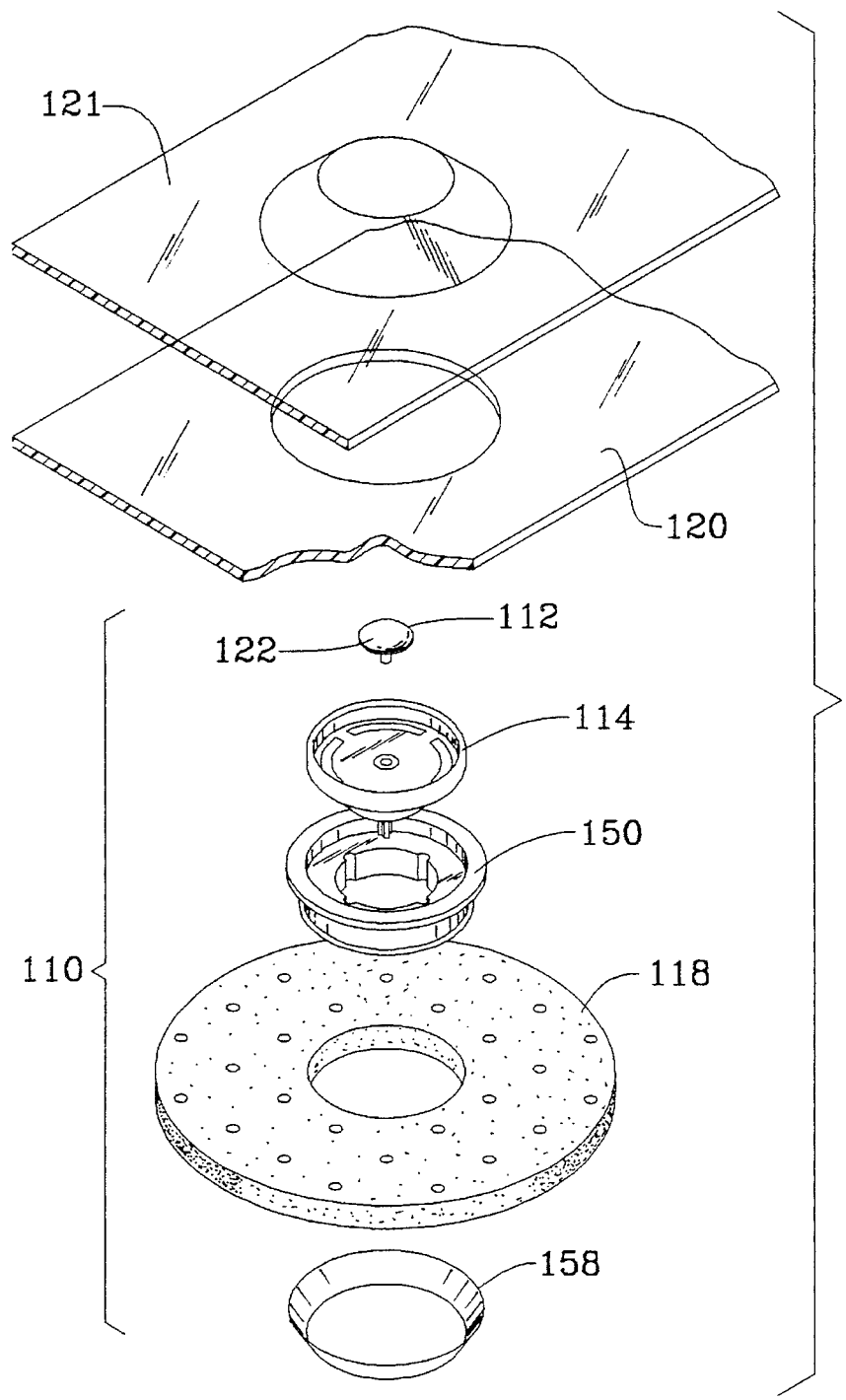
FIG. 7 is an exploded perspective view of the electrode of the present invention.
Figure 10:
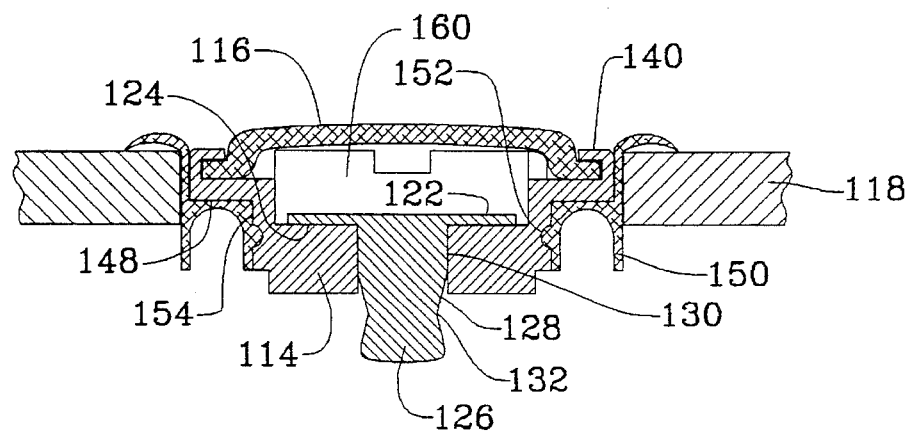
FIG. 10 is a cross sectional view of the electrode of the present invention taken generally along lines 10—10 of FIG. 8.

In the preferred form of the present invention, the center member 112 is preferably a plastic carbon member having a thin silver plated layer thereon which has been treated with silver chloride to enhance ion flow therethrough as well as to form a low impedance point of connection with the wires (not shown) of the electrode. As shown in FIGS. 7 and 10, the center member 112 of the present invention includes a generally flat first surface 122 with a circularly shaped outer circumference having a diameter which is greater than the diameter of the aperture 134 in the housing 114 as described below. The second surface 124 of the center member 112 includes the post member 126 extending therefrom. The post member 126 includes tapered surface 128 which extends from the second surface 124 of the center member 112. The tapered surface 128 includes a slight rib 130 thereon and decreases in circumference to form a snap area 132 on the post member 126 which is contacted and engaged by a snap type of electrode connector (not shown). The rib 130 is shaped to frictionally contact a portion of the housing 114 described below. Unlike the prior art post member 52 shown above in FIGS. 1–4, the post member 126 of the present invention is preferably not hexagonally or otherwise particularly shaped to receive reciprocal motion from the applicator gun 70 (FIG. 4) thereon.

Figure 9:
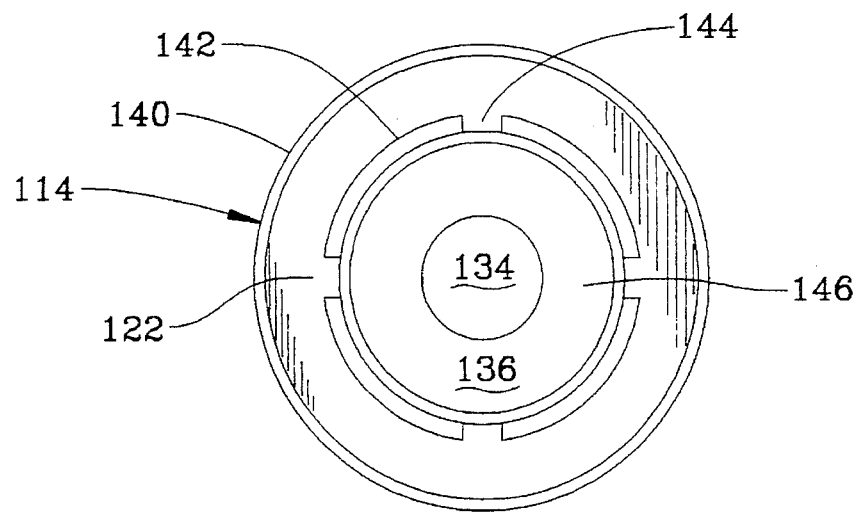
FIG. 9 is an elevated view of the electrode as illustrated in FIG. 8 with the mesh screen removed.
Figure 11:
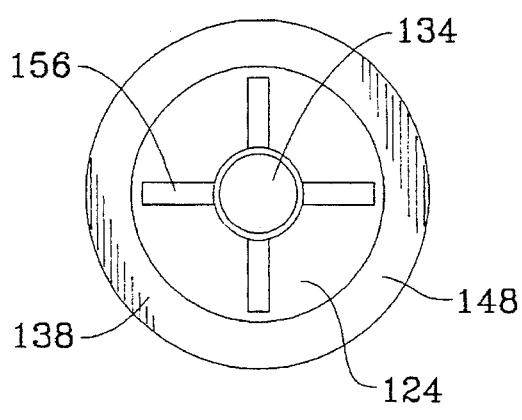
FIG. 11 is an elevated view of the electrode of the present invention showing the post member and second surface of the housing.

The circumferential housing 114 of the present invention is preferably formed of a rigid plastic or similar material. As shown in FIGS. 9–11, the housing 114 includes an aperture 134 extending therethrough and first and second surfaces 136 and 138 respectively. The aperture 134 is formed to frictionally receive the center member 112 therein. The first surface 136 of the housing 114 is best shown in FIG. 9. The first surface 136 includes an outer circumferential rib 140 which forms the outer periphery of the housing 114 and an inwardly positioned annular ring shaped surface 142 having a plurality of channels 144 formed therein. During assembly, the circumferential rib 140 is crimped or otherwise formed to retain the screen member 116 thereon as shown in FIG. 10. A recessed area 146 is also located inwardly of the annular surface 142 to surround the aperture 134 and receive the first and second surfaces 122 and 124 of the center member 112 therein.

The second surface 138 of the housing 114 is best shown in FIGS. 7 and 11. The second surface 138 includes a generally flat contact surface 148 which is shaped to receive a portion of the retaining ring 150 thereagainst in a manner similar to the contact between the collar 14 and the conductive member 16 as shown in FIG. 2. The sidewall surface 154 of the housing 114 extends outwardly from the contact surface 148 and includes a circumferential recess 152 therein. The circumferential recess 152 is sized to frictionally receive a portion of the retaining ring 150 therein while allowing the housing to rotate with respect to the retaining ring 150. A plurality of radially extending ridge members 156 extend between the aperture 134 in the housing 114 and sidewall surface 154 of the housing 114 to enable the coupler 88 of the applicator gun 90 to contact the ridge members 156 and impart rotational movement to the housing 114. As with the collar 14 shown in FIG. 2, the retaining ring 150 of the present invention extends between the outer surface of the housing 114 and the sheet member 118 to retain the housing 114, center member 112 and screen member 116 in the sheet member 118 while allowing rotational movement between the housing 114 and retaining ring 150. Additionally, the snap ring 158 of the present invention is positioned between the outer surface of the retaining ring 150 and the sheet member 118 to prevent rotational movement between the sheet member 118 and the retaining ring 150.

The screen member 116 of the present invention is preferably constructed of a flexible silicon carbide or other abrasive material. The screen member 116 is sized so that when the outer circumference of the screen member 116 is positioned generally inwardly from and adjacent to the crimped outer circumferential rib 140, the screen member 116 contacts the annular ring surface 142 of the housing 114 and is bowed slightly outwardly therefrom. This orientation is particularly useful to provide consistent abrasion of the skin of the patient because if the user of the applicator gun presses too hard during the preparation of the skin of the patient, the screen member 116 will flex to decrease the abrasion of the skin. This is in contrast to the electrode shown in FIGS. 5 and 6 wherein the mesh screen 104 is rigidly held in place by the post members 106.

The flexibility of the screen member 116 and the orientation of the screen member 116 with respect to the housing 114 and center member 112 are also particularly important during the use of the electrode. The electrolyte gel (not shown) is placed in the housing 114 to fill the space between the first surface 136 of the housing 114, the first surface 122 of the center member 112 and the screen member 116. When the electrode is applied to the skin of the patient, the sheet member 118 encircles the periphery of the housing 114 such that the electrolyte gel is trapped therein. During certain procedures such as ECG stress tests, the patient is exercising or otherwise moving around. This movement causes the skin which is in contact with the various electrodes to stretch or contract according to the movements of the patient. During this movement, the skin may press against or move away from the prior art electrode shown in FIGS. 5 and 6 because of the rigid support provided to the mesh screen 104 by the post members 106. This movement between the electrode and the skin of the patient causes muscle artifact and may even break the signal between the patient and the recording device. During use of the electrode of the present invention, the electrolyte gel forms a gel column in the electrode which responds to the movement of the skin of the patient to ensure that the electrolyte gel maintains electrical contact between the skin of the patient and the center member 112. The area between the circumferential rib 140 and the annular surface 142 on the first surface 136 of the housing 114 functions basically as a reservoir area 160 for the electrolyte gel in the present invention. For example, if the skin of the patient presses against the slightly flexed or raised center of the mesh screen, the electrolyte gel is pushed back into the recess of the housing and is forced to flow to the outer periphery of the housing 114 through the channels 144 in the annular surface 142 to the reservoir area 160 of the housing 114 between the circumferential rib 140 and the annular surface 142. When the skin of the patient draws away from the electrode, the electrolyte gel is drawn from the reservoir area 160 of the housing 114 through the channels 144 and into the recessed area 146 to ensure that a continuous column of electrolyte gel extends between the skin of the patient and the center member 112.

Figure 12:
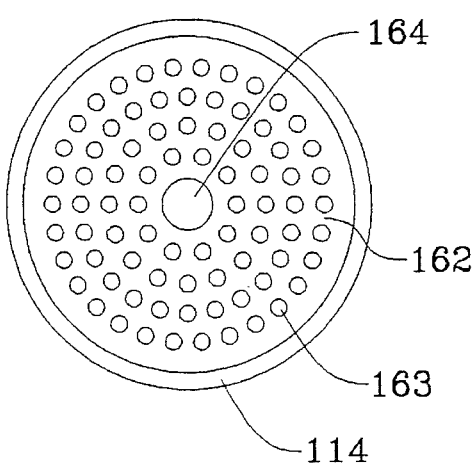
FIG. 12 is an elevated view of an alternate embodiment of the present invention.

FIG. 12 is illustrative of a further embodiment of the present invention wherein the screen member 116 of FIGS. 7–11 is replaced with a flexible member 162 having a plurality of spaced apart holes 163 extending therethrough which are generally larger than the openings in the screen member 116 and which also includes a centrally located and larger center hole 164. The electrode of this embodiment operates generally in the same manner as the preferred embodiment; and, therefore, like numbers have been added to like members, and the features common to each embodiment are not separately repeated herein.

The foregoing is intended to be illustrative of the currently preferred forms of the present invention which is defined by the following claims.

What is claimed is:

1. A disposable medical electrode for improving the quality of biopotential event detection by minimizing motion artifacts arising from the skin of a patient, said electrode comprising:

conductive means capable of detecting and transmitting biopotential events for recording;

abrasive means operatively associated with said conductive means for abrading the epidermal layer of the skin of the patient;

holding means associated with said conductive means for securing the electrode to the skin of the patient with said abrasive means in contact with the skin of a patient, said abrasive means is spaced apart from said conductive means and is movable relative to the skin and said conductive means upon application of the electrode to the skin of the patient; and said holding means including a sheet member and said sheet member having an adhesive material thereon to secure the electrode to the skin of the patient while allowing said abrasive means to be movable with respect to the skin of the patient and said sheet member.

2. The electrode of claim 1 wherein said abrasive means and said conductive means are rotatable relative to the skin of the patient and said sheet member.

3. The electrode of claim 2 wherein said conductive means is a radiolucent member.

4. The electrode of claim 1 wherein said conductive means is formed of a radiolucent carbon based material.

5. The electrode of claim 4 wherein said conductive means has a silver plated layer thereon.

6. The electrode of claim 4 wherein said conductive means has been treated with silver chloride thereon to increase the flow of ions therethrough.

7. The electrode of claim 1 wherein said electrode further includes a housing therein and wherein said housing engages said conductive means and said abrasive means and is rotatable with respect to said holding means.

8. The electrode of claim 7 wherein said housing is formed to include a reservoir area between said abrasive means and said housing for the receipt of an electrolyte gel therein.

9. The electrode of claim 7 wherein said electrode further includes an electrolyte gel therein and said electrolyte gel forms a gel column in said housing such that gel flows into or out of said reservoir area in response to the movement of the skin of a patient adjacent to said abrasive means.

10. The electrode of claim 1 wherein said abrasive means is a flexible member which flexes in response to the skin of the patient surrounding said electrode.

11. The electrode of claim 10 wherein a surface of said abrasive means is oriented adjacent to the skin of the patient in use and is flexible and generally convexly oriented with respect to said conductive means.

12. A disposable medical electrode which allows preparation of the skin of a patient to reduce motion artifacts after application of the electrode to the skin of the patient, said electrode comprising:

an electrically conductive member having a surface facing the skin of a patient in use when the electrode is adhered to the skin;

a retaining member in operative engagement with said conductive member;

a flexible sheet member secured to said retaining member and said sheet member having an adhesive thereon for adhering the electrode to the skin of the patient;

a flexible abrasive member in operative engagement with said retaining member and spaced apart from and movable relative to said conductive member;

an electrolyte gel in operative contact with said conductive member and the skin of the patient when the electrode is secured to the skin of the patient, said conductive member and abrasive member being rotatable relative to the skin and said retaining member and wherein said sheet member adheres the electrode to the skin of the patient to enable the abrasion of the portion of the skin in contact with the abrasive member to minimize motion artifact while forming a reservoir area of said gel generally between said abrasive member and said conductive member.

13. The electrode of claim 12 wherein said abrasive member is a resilient screen shaped member with said electrolyte gel operatively interposed between said screen shaped member and said conductive member.

14. The electrode of claim 12 wherein said conductive member is circular and provided with a stud for operative connection to an electrically responsive recorder and wherein a housing member is further included having a collar with an annular opening provided with a flexible wall thereabout receiving said conductive member therein while allowing said conductive member to be rotated relative to said retaining member on application of a predetermined amount of torque.

15. A disposable pre-gelled medical electrode which reduces motion artifacts, said electrode comprising:

an electrically conductive member having a first surface oriented to face the skin of the patient when the electrode is placed on the skin of the patient in use and an opposing stud on a second surface thereof for connection to an external electrically responsive monitor;

an electrically non-conductive housing retaining said conductive member therein, said housing including an annular opening receiving said conductive member therein;

a flexible abrasive member operatively retained by said housing and including a gel in contact with said conductive member, said abrasive member being movable relative to said conductive member and said abrasive member and said housing further forming a gel reservoir area therebetween such that when said abrasive member is pressed against the skin of the patient said gel flows into said reservoir area; and a sheet member operatively associated with said housing and having an adhesive material thereon to secure the electrode to the skin of the patient while allowing said abrasive member to be movable with respect to the skin of the patient and said sheet member.

16. The electrode of claim 15 wherein said reservoir area is oriented with respect to said abrasive member and said housing such that said gel flows from said reservoir area as the skin of the patient moves away from said abrasive member.

17. The electrode of claim 15 wherein said abrasive member is spaced apart from said conductive member and said gel is positioned between said abrasive member and said conductive member in a first position of said abrasive member and wherein at least a portion of said gel is located between the skin of the patient and said abrasive member in a second position of said abrasive member.

18. The electrode of claim 15 wherein said abrasive member is oriented with respect to said housing to flex in response to contact with the skin of the patient.

* * * * *